United States Patent [19]

Lawler, Jr.

[11] Patent Number: 4,820,281

[45] Date of Patent: Apr. 11, 1989

[54] DROP VOLUME MEASUREMENT SYSTEM

[75] Inventor: Casimir E. Lawler, Jr., Eden Prairie, Minn.

[73] Assignee: Ivy Medical, Inc., Minneapolis, Minn.

[21] Appl. No.: 52,470

[22] Filed: May 21, 1987

[51] Int. Cl.⁴ .................... A61M 5/165; A61M 31/00
[52] U.S. Cl. ........................................ 604/253; 604/65
[58] Field of Search ........................ 604/65, 251, 253

[56] References Cited

U.S. PATENT DOCUMENTS

| | | | |
|---|---|---|---|
| 4,173,224 | 11/1979 | Marx et al. | 604/65 |
| 4,328,801 | 5/1982 | Marx et al. | 604/253 |
| 4,432,761 | 2/1984 | Dawe | 604/253 |
| 4,432,762 | 2/1984 | Dawe | 604/253 |
| 4,623,331 | 11/1986 | Cewers et al. | 604/253 |
| 4,635,281 | 1/1987 | Jones | 604/253 |

Primary Examiner—John D. Yasko
Assistant Examiner—Kathleen A. Daley
Attorney, Agent, or Firm—Moore & Hansen

[57] ABSTRACT

Apparatus and method for measuring the volume of a drop, and with a series of drops the volumetric flow rate of a fluid utilizing a vertically oriented, transparent drop chamber through which the fluid is directed in drop form. A plurality of drop sensors positioned adjacent to the drop chamber in vertically spaced relation to each other emit signals in response to the detection of the entrance and exit of each drop to and from separate sensor fields preferably established by light emitting sources. The drop sensors are connected to control circuitry incorporating an electronic processor programmed to determine volumetric flow rate in response to drop dimension and drop rate signals received from the drop sensors. The drop size in terms of the vertical dimension of each drop in the direction of gravity flow through the drop chamber is determined by measuring the time it takes a drop to pass through each and both of the two sensor fields. Timers used for this purpose are triggered by the aforesaid sensor signals. The volume of each drop is electronically calculated as a function of the drop vertical dimension, and drop volume and drop rate are multiplied to determine volumetric flow rate.

17 Claims, 4 Drawing Sheets

DROP VOLUME MEASUREMENT SYSTEM

BACKGROUND OF THE INVENTION

This invention is directed to the measurement of volumetric fluid flow rate in applications where the flow rate must be accurately determined. In particular, the volume measurement system disclosed herein has been designed to be especially useful in the improved delivery of intravenous (IV) fluids to patients.

The intravenous delivery of fluids to patients is normally carried out with a disposable kit or administration tube set. Such a tube set conventionally comprises a length of flexible rubber or plastic tubing attached at its bottom end to a needle injected into the patient, and connected at its top end to a transparent drip chamber, with the drip chamber being connected through a hard, hollow plastic spike at its upper end to an IV fluid container in the form of a bag or bottle. The transparent drop chamber permits visual determination of the presence of flowing fluid, as well as the ability to sense the drop rate.

The cost of medical care in the United States has steadily increased over recent years. High priced medical equipment required in hospitals has been a major factor in causing rising medical costs. Such equipment includes devices for the intravenous introduction of fluids to hospital patients. Such IV systems fall into the two general categories of gravity feed and pressurized feed. The gravity feed systems rely on gravity to generate the flow of IV fluid from the supply bag or bottle through the drip chamber and tubing to the injection needle. A clamp or other adjustable restrictive device is normally provided on the tubing below the drip chamber, so as to selectively restrict the tubing and adjust the flow rate. Photoelectric sensors, in combination with a light source, have been used adjacent to the drip chamber to sense the drops and to emit a signal used to determine the drop rate. This drop rate may be used by a controller to operate the drive motor of sophisticated clamping devices. These sophisticated clamping devices in the form of motor operated clamps and valve mechanisms are presently used to automatically control the rate of flow through IV tubing by selective restriction of the tubing, and thus of the flow passage.

U.S. Pat. Nos. 3,700,904 and 3,604,419 disclose such electromechanically operated controllers for IV tubing. The latter patent discloses a closed loop servo mechanism for an electromechanical controller in combination with a drop rate detector. U.S. Pat. No. 4,191,184 discloses an IV controller with particularly designed valve members actuated in response to variations in drop rate of the IV fluid. U.S. Pat. No. 3,450,153 discloses a drop rate sensing device which detects the timing of each individual drop pulse and controls the IV fluid rate in response to a detected timing error, in contrast with systems which control flow rate by way of drop pulse count averaging.

U.S. Pat. No. 4,493,710 discloses an electromechanical controller which utilizes specially designed clamping members to place the IV tubing in tension as a means of restricting the internal flow passage within the IV tubing. The clamping members are moved by a drive motor which is activated by a controlling device responsive to signals generated by a drop rate sensor.

In addition to the use of controllers of the aforesaid type on gravity feed systems, infusion pumps have been developed for providing pressurized flow of IV fluid to a patient. Presently there are two types of positive displacement IV pumps; diaphragm/piston and peristaltic. Such pumps are used to accurately maintain IV fluid flow, and are both expensive to purchase and operate. The initial infusion pump price of up to $3,000.00 is soon exceeded by the operating costs of up to $900.00 per year due to the specialized tube sets and equipment used with the pump. There is thus a need for a low cost, high quality infusion system that is also inexpensive to operate.

As with other types of pumps, some peristaltic pumps are volumetric pumps, delivering fluids in measured volumes. Peristaltic pumps accomplish this by crimping the IV tubing of a known inner diameter at two points, trapping and dispensing a known volume of fluid. Peristaltic pumps are noninvasive with respect to the administration set, and are frequently employed. U.S. Pat. Nos. 4,217,993 and 4,213,454 disclose peristaltic pumps with a restriction device downstream of the pumping mechanism. This restriction device provides periodic back pressure against which the pump must operate, so as to help maintain the known inner diameter of the tubing used.

Peristaltic pumps are commonly driven by stepper motors which are powerful enough to force fluids through the IV tubing while maintaining a constant flow rate against the back pressures encountered in the human body. Based on the known inner diameter of a specific pump manufacturer's tube set, the microcontrollers in these pumps are calibrated in terms of a volume output per motor step. An operator simply selects rate of fluid delivery, and the controller determines the stepping rate of the motor. When started, the motor moves at a constant rate, thereby providing a constant flow regardless of back pressure.

Most pumps do not utilize standard IV tube sets because of the errors which such standard tube sets introduce into the volumetric flow. In order to maintain a volumetric accuracy of greater than or equal to 95 percent, IV pumps conventionally utilize special IV tube sets. The tubing for such sets is held to a close tolerance of down to ±0.001 inches on its inner diameter of about 0.1 inches, in contrast with tolerances of up to ±0.005 or more inches on standard tubing of the same inner diameter. Such greater tolerances guaranty an unacceptable volumetric error of at least plus or minus ten percent from one standard tube set to another. Also, because not all manufacturers use the same inner tubing diameter, and all conventional peristaltic pumps are specifically calibrated for a given manufacturer, all tubing sets are pump and manufacturer specific. Using tube sets from manufacturers other than the pump manufacturer can result in greater than ±10% volumetric flow rate errors. Such special tube sets also normally have a particularly designed mid section of tubing in the IV set where the pump operates. This section of tubing is more resilient than the surrounding sections, and its inner diameter is closely controlled as stated. These factors contribute to the high price of specialized tube sets.

Most pump manufacturers do not utilize standard IV tube sets in peristaltic pumps also because such tube sets are less resilient than specialized tube sets. As a result, standard tube sets fatigue faster and do not recover as completely after being crimped as do specialized tube sets. This poor resiliency has the effect of reducing the inner diameter of the tubing over time, which alters the actual output volume and decreases the accuracy of the pumping system. As a result patients may be given too much or not enough medication.

In order to fill the need for a new infusion system with a low operating cost, an inexpensive and accurate method to measure volumetric flow rate through any type of standard IV tubing is needed. A sensing technique and apparatus which measures volumetric fluid flow rate independently of IV tubing inner diameter and wear has been developed to meet that need.

When incorporated into an IV pump or controller this new volumetric flow measurement system will work with any tube set from any manufacturer while maintaining a high volumetric flow rate accuracy. This unique sensing technique is based on determining the volume of fluid drops as they fall through the drip chamber of an IV-type tube set. Drip rate is monitored along with drop volume, so that actual volumetric flow rate may be calculated and used to control the operation of a pump or controller. U.S. Pat. No. 4,105,028 discloses an intravenous fluid delivery system which purports to provide an indication of the size of fluid drops detected by a drop sensor. A clamping type of flow controller periodically impinges the IV tubing at predetermined frequencies in direct response to the size of formed drops. However, drop size alone is used to control the flow rate, and not total flow volume. Drop volume is not computed in this disclosed system, but rather only a minimum size dimension is monitored. Furthermore, the controller disclosed in that patent is invasive to the administration set in that it requires some controlling or sensing surface to pass into the tube set and come in direct contact with the fluid being delivered. A special drip chamber is also required so as to control the formation of drops in response to size variations, thereby increasing the cost of the tube set. This drip chamber is part of a special tube set which must be utilized. The drip chamber incorporates electrodes with which the drops must be in direct contact in order for the system to function as intended.

An article by B. J. Azzopardi, "International Volume of Heat and Mass Transfer," Volume 22, No. 9, September 1979, discloses the use of two drop detectors, one below the other, in combination with light beams and fiber optics to determine the size, velocity, and frequency of fluid drops traveling through the sensor fields. This system apparently requires that the drops be smaller in size than each sensor field, and thus would present difficulties in application to IV systems where relatively large fluid drops are encountered.

U.S. Pat. No. 4,583,975 issued on Apr. 22, 1986 discloses a piezoelectric drop counter and method wherein piezoelectric film strips are used to sense and generate signals in response to the impingement of drops onto a surface of accumulated fluid in a drip chamber.

These disadvantages of previously known drop sensing devices are overcome in the improved drop volume measurement system disclosed herein.

BRIEF SUMMARY OF THE INVENTION

The volumetric flow measurement system disclosed herein is particularly characterized by its ability to utilize any standard IV tube set in a noninvasive manner while maintaining minimal initial costs and low operating costs, particularly when used with an infusion control device. The high operating cost of infusion control devices normally associated with the need to replace disposable, special tube sets has been eliminated by removing the need for special tube sets.

A primary objective has been to provide an inexpensive and very accurate, noninvasive, volumetric fluid flow measurement system. A secondary objective has been to incorporate this flow measurement system into an inexpensive and accurate infusion control device used to introduce intravenous fluids by positive displacement or mechanized control into human beings.

These basic objectives have been realized by utilizing sensing devices to accurately measure the vertical drop size as well as drop rate. From drop size, drop volume may be determined. The product of drop volume and drop rate is volumetric flow rate. This rate may be used to accurately regulate a flow controlling mechanism to conform the flow rate to a predetermined value for particular applications.

In a preferred embodiment, a plurality of drop sensing devices are used in such a way in conjunction with a drip chamber as to be able to measure drop size, from which drop volume may be determined. As used herein, drop size means the vertical dimension of a drop in the direction of gravity flow. As hereinafter set forth, the preferred drop model of a sphere assumes this vertical size dimension to be the drop diameter.

An electronic processor mechanism, preferably in the form of a microprocessor or microcontroller, is effectively utilized to determine volumetric flow rate in response to drop size and drop rate signals received from the sensors. This processor also controls the movement of a drive motor which operates a flow regulating device such as a peristaltic pump or flow limiting controller. Any type of controller or pumping mechanism, be it linear or rotary peristaltic or other, can be regulated in response to the information provided by the disclosed volumetric flow measurement system.

Control of the flow rate is best achieved by the use of a closed loop, or feedback, type of control system. This system incorporates the drop size and drop rate detection system, the electronic processor, and the flow control mechanism for the IV fluid to alter the actual volumetric flow rate to match the desired volumetric flow rate.

A particularly advantageous feature resides in the drop sizing technique utilized. Because of errors in drip chamber construction and the fact that drop size is fluid, pressure and drop rate dependent, counting drops alone is not enough. By measuring the time it takes a drop to pass through two sensor fields, the size of the drop can be determined. The two sensor fields are preferably in the form of light beams utilized in combination with photoelectric cells positioned adjacent to the drip chamber in vertically spaced planes. Because the sensor fields are projected into the drip chamber from the outside, the system is totally noninvasive to the tubing and may be used with any IV set which has a drip chamber.

Because the drops fall for only a very short distance in the enclosed area of the drip chamber, in the absence of wind resistance, and because of the relatively strong surface tension of fluids, the drops are relatively spherical and the drop size, determined as mentioned above, is the diameter of the spherical drop. From this drop diameter, the drop volume may be easily calculated. The actual flow rate delivered may then be determined using this drop volume and the drop rate. Maintaining a record of accumulated volume and elapsed time, an overall volumetric flow rate may be derived. This computed actual output of the flow control system as determined by an electronic processor, may be compared to a desired output value and used to control the drive motor for the flow control system. The control process may take on a variety of forms, from simple proportional control to proportional-integral-derivative (PID) control, depending on the desired system responses.

In its optimal configuration the whole system is operated by a microprocessor or microcontroller and some related support circuitry. The multiple sensor fields traversing the drip chamber are created by multiple sets of vertically spaced infrared (IR) light emitting diodes (LED) and IR detectors. The support circuitry connected to the output of the IR detectors preferably utilizes comparators to convert the analog outputs of the drop sensors to digital signals, as well as counter/timers and preprocessing logic gates to trigger the counter/timers appropriately. The microprocessing device also preferably controls the output circuitry which operates the flow controlling drive mechanism.

The support circuitry connected to the output from each IR detector preferably starts with Schmitt Trigger type comparators. Each comparator functions to enable a counter running on a fast, known clock. The comparators also alert the main processor to read the counters and to determine drop rate. The main processor uses the outputs of the counters to compute the drop volume, which in turn is used with drop rate to determine volumetric flow rate. The processor then compares the computed volumetric flow rate to the previously stored, desired value. If there is sufficient error between actual and desired volumetric flow rates, the electronic processor adjusts the flow control mechanism. The processor makes this adjustment by outputting a value to the flow control mechanism drive circuitry. This control circuitry may be composed of a variety of elements, including the preferred stepper motor controller integrated circuit which converts signals given to it by the processor into the phased signals used to operate a stepper motor.

A variety of means with which to operate the flow controlling mechanism may be used with this new volumetric flow measurement system. For an infusion controlling device, the preferred drive motor for the flow restricting mechanism is a stepper motor. Also for an infusion controlling device, the actual preferred pumping mechanism may be any type of positive displacement device, such as a linear or rotary peristaltic mechanism. Because the volumetric flow rate is monitored and explicitly determined, as opposed to being assumed, any type of motor or pumping mechanism or flow rate regulator that can be controlled may be used.

The apparatus and methods disclosed herein may be used as a fluid volume delivery measuring system in various applications other than for the delivery of intravenous fluids.

These and other objects and advantages of the invention will be readily apparent as the following description is read in conjunction with the accompanying drawings wherein like reference numerals have been used to designate like elements throughout the several views.

DESCRIPTION OF THE PREFERRED EMBODIMENT

Figures 1, 2, 3, 8:
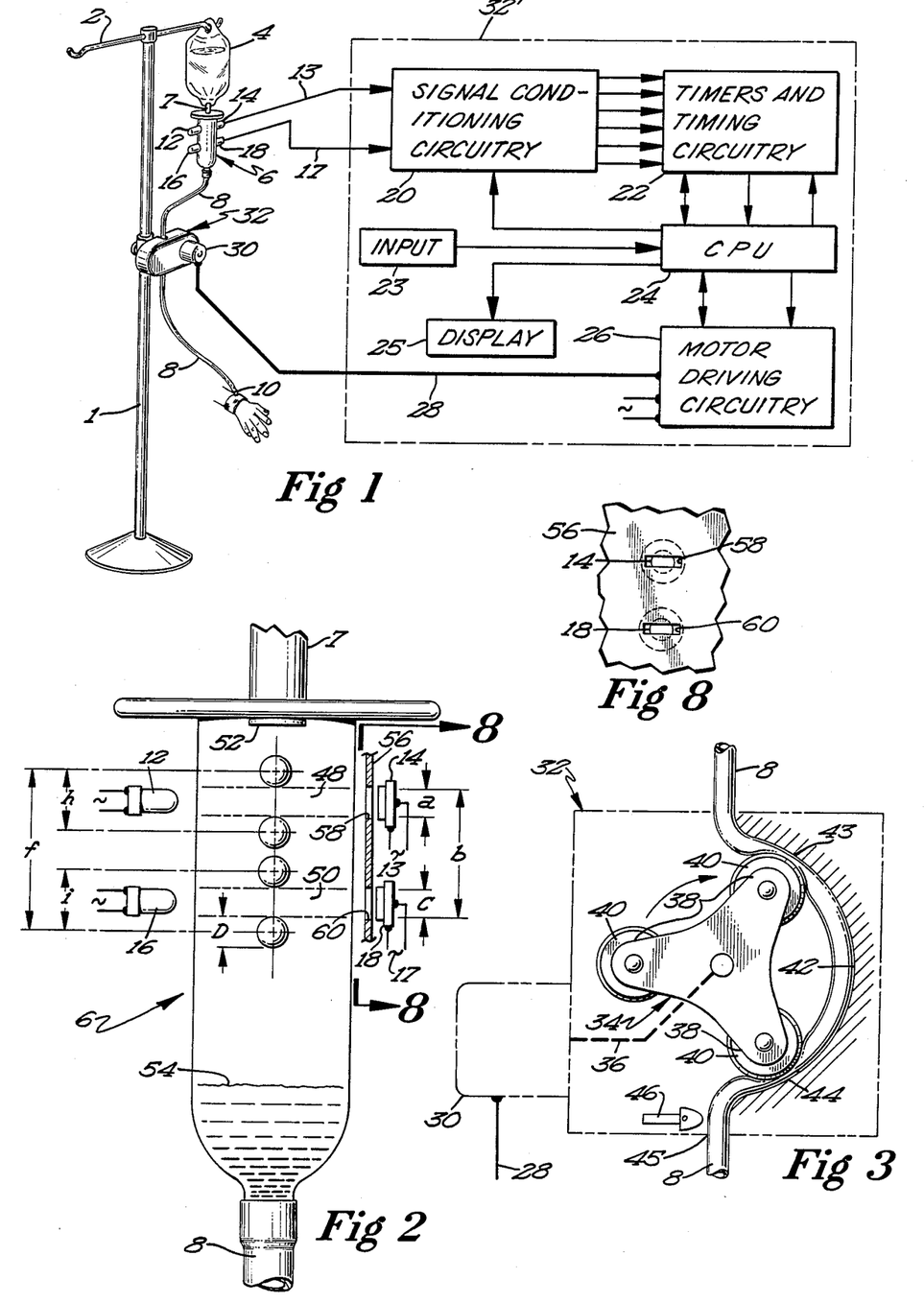
FIG. 1 is a partially diagrammatic perspective view depicting the volumetric flow measuring apparatus of this invention.
FIG. 2 is a fragmentary, enlarged diagrammatic view showing the photoelectric cell drop sensing mechanism on the drip chamber.
FIG. 3 is a schematic view of a rotary peristaltic pump of the type which may be utilized in the fluid delivery system of an infusion control device using this invention.
FIG. 8 is an elevation view of a form of masking strip which may be used to provide the desired field defining slits for the drop sensing devices.

Referring now to the drawings, there is shown in FIG. 1 a standard IV administration set for the delivery of fluid intravenously to a patient, incorporating the improved volumetric flow rate measuring and controlling apparatus of this invention. The administration set is mounted on an IV pole 1 having a hanger 2 at its top end from which a supply bottle or bag 4 of the fluid to be delivered intravenously is suspended as shown. The bottom, outlet end of fluid container 4 is connected by way of a flow passage 7 to the drip orifice at the upper end of a drop chamber 6. Flow passage 7 normally takes the form of a hard, hollow plastic spike. Drip chamber 6 is transparent for drop detecting and measuring purposes as hereinafter set forth.

The bottom end of drip chamber 6 is connected to a flexible rubber or plastic tube 8. Flexible delivery tube 8 is directed through a flow regulating device mounted on IV pole 1 as shown. Such a device is generally indicated by reference numeral 32, and may have a drive motor 30. The flow regulating device functions to regulate the flow of intravenous fluid through delivery tube 8 connected through an injection needle 10 to a patient as shown. Various forms of flow regulating mechanisms 32 may be utilized, as hereinafter set forth.

For purposes of measuring the vertical drop size and drop rate, drip chamber 6 is provided with two sets of sensing devices which create horizontal sensor fields or planes through which drops pass vertically. The first sensing field may be generated by a light emitting source 12, preferably in the form of infrared light emitting diode(s) (IRLED), and aligned infrared (IR) detector(s) 14. Spaced vertically below this sensor field is a second sensor field also preferably generated by infrared emitting diode(s) 16, and horizontally aligned infrared detector(s) 18. These sensor fields are explained more fully with respect to FIG. 2.

The output signals from the two sensor fields are connected as shown in FIG. 1 through electrical leads 13 and 17 to control circuitry. Such control circuitry is generally indicated in FIG. 1 to include its basic segments comprising signal conditioning circuitry 20, timers and timing circuitry 22, a central processing unit (CPU) 24, flow volume and data setting and display means 25, and motor drive circuitry 26. An input device 23, such as a keyboard, is preferably utilized to input data such as desired volumetric flow rate and desired total fluid volume to CPU 24. Output signals from the motor drive circuitry are directed through conductor lead 28 to motor 30 in order to provide drive signals to adjust the drive motor 30 as necessary to maintain a predetermined flow rate by way of flow regulator 32. Preferably, the majority of the control circuitry, generally indicated by reference numeral 32,, is incorporated in a microprocessor peripheral device contained within the housing of flow regulating device 32.

It is contemplated that various types of flow regulating devices 32 may be utilized on the IV fluid delivery tubing 8. A motor driven, flow restricting type of controller as disclosed in U.S. Pat. No. 4,493,710 owned by the common assignee herewith would be satisfactory. Such a control device utilizes a pair of clamping jaws as disclosed in the aforesaid patent to selectively restrict and enlarge the flow passage through an IV delivery tube.

Alternatively, and preferably, when positive displacement flow of IV fluid to a patient is desired, an infusion pump may be utilized. Such a pump preferably takes the form of a peristaltic pump as shown in FIG. 3. The peristaltic pump 32 is of known design for delivering fluids. The disclosed rotary type pump is comprised of a rotor 34 connected by a drive shaft 36 to drive motor 30, as shown in FIG. 3. Rotor 34 may be comprised of a plurality of radially extending rotor arms 38, which carry guides, or rollers 40 at their outer ends. The flexible IV delivery tube 8 is directed into the housing of pump 32 so as to be guided along curved pump housing wall 42. As rotor 34 revolves, the rollers 40 sequentially pinch or crimp flexible delivery tube 8 at two distinct and separated locations 43 and 44 along the curved wall 42 of the pumping chamber, thereby trapping a volume of fluid between the two crimped points. Because the rotor arms 38 are a predetermined distance apart, the actual volume trapped by the peristaltic mechanism may be estimated. The accuracy of the estimation of the trapped volume depends on the accuracy and consistency of the inner diameter of the tubing. Over time the inner diameter of the tubing may change and the actual volume trapped will also change. This trapped fluid is delivered to discharge end 45 of the pumping mechanism 32, as the drive motor 30 rotates the rollers 40 over the flexible tubing 8. A guide 46 may be used to create localized pressure increase between the rollers 40 and the discharge end 45 of pump 32.

Linear types of peristaltic pumps may also be utilized.

As peristaltic pumps operate, the flexible tubing on which they act is continually compressed and released, thereby fatiguing the tubing. The tubing must have good resilience and elastic memory in order to withstand the effects of this fatigue. The resilience of a plastic tube determines the rate at which the tubing regains its original shape after experiencing tensive or compressive forces. The rate at which the tubing regains its shape increases with resilience. The elastic memory of tubing determines how close to its original shape the tubing will return as it recovers from tensive or compressive forces. The tubing will fully regain its original shape if it has good elastic memory. The actual volume trapped in a tube between the guides or rollers 40 of a peristaltic pump will decrease with increasing tubing fatigue, if the tubing has less than perfect resilience and/or poor elastic memory. To improve the accuracy of volume "measurements" and delivery, peristaltic pump manufacturers require the use of special IV tube sets utilizing a section of tubing that has a high degree of resilience and good elastic memory. It is on this section of tubing, that the peristaltic pumping rollers or guides operate. This section may be made of a silicone enriched rubber and may have a much closer tolerance on its inner diameter than standard IV tubing. Manufacturing this special tubing and bonding it to the standard IV tubing, often made of a polyvinylchloride compound, while maintaining sterility, is three to five times more expensive than manufacturing standard IV tube sets. However, the volumetric accuracy of presently available peristaltic infusion pump systems resides in these specialized tube sets.

The output volume per unit time of presently available peristaltic pump systems may be determined by dividing the volume trapped between the guides or rollers 40 by the number of motor steps required to dispense the fluid, then multiplying this quotient by the frequency at which the stepper motor is driven. Presently used controlling circuitry need only convert the desired flow rate into a motor rate. The special section of tubing in a specialized tube set for a peristaltic pump is resilient enough to trap a reproduceable volume of fluid, within an acceptable error boundary, for 12 to 24 hours. The actual output volume and/or volumetric flow rate are never determined or used to control presently available pumps. The volumes trapped and delivered are assumed to be consistent volumes. Because the actual output of the system has no effect on the control of the driving mechanism, present pump systems are open loop control systems. This type of control places the burden of volumetric flow accuracy on the resilience, elastic memory, and inner bore tolerance of the IV tubing used.

Standard IV tubing has neither the close bore tolerance, the resilience, nor the elastic memory required for accurate IV administration with presently available pump systems. The loose inner diameter tolerances of standard IV tube sets can cause ±10% or more volumetric error. Standard IV tubing also does not regain its original shape after it is pressed, because of its relatively poor elastic memory and low resilience. The volume trapped inside the tubing, decreases as the tubing flattens. Unless the rate of the decrease in volume is known exactly, the volumetric accuracy of available infusion systems will also decrease as the tubing flattens. The rate at which the volume decreases cannot be known exactly because it depends on the rate of the pumping mechanism and the material characteristics of the specific tubing used. The exact error due to the poor elastic memory is rendered academic by the ±10% volumetric error caused by the loose inner diameter tolerances. This ±10% error is twice the maximum percent error suggested by the Emergency Care Research Institute for Emergency (ECRI) for "Special Care Equipment."

The volumetric flow measurement technique disclosed herein overcomes the aforesaid problems by explicitly determining the actual volume and volumetric flow rate of the fluid being infused. This volumetric flow rate measurement technique may be used in conjunction with a means of fluid delivery to create a closed loop control system. In such a closed loop control system, the actual volumetric flow rate may be compared to the desired flow rate and used to alter the operation of the driving motor.

In FIG. 2 there is shown on an enlarged scale a drip chamber 6 with the preferred sensor devices and sensor field arrangement. The first or upper sensor device is shown with its light emitting source in the form of light emitting diode(s) 12 and infrared detector(s) 14. A first sensor plane, or field, 48 is created by light source(s) 12. Spaced vertically below sensor field 48 a determined distance is a second sensor field 50 established by a second light source in the form of light emitting diode(s) 16 and corresponding infrared detector(s) 18 in horizontal alignment therewith. The light sources 12 and 16 are positioned as shown so as to provide a pair of vertically spaced sensor fields extending horizontally or transversely across drip chamber 6.

It should be noted that there are a variety of sensor device configurations that may generate the two desired sensor fields. One such configuration places the light emitting diodes 12 and 16 and their corresponding detectors 14 and 18 on the same side of the drip chamber 6. A drip orifice 52 is provided at the top of the drip chamber, at the outlet of fluid passage 7 leading from fluid container 4.

Appropriate means may be utilized as required to prevent sensor fields 48 and 50 from interfering with each other. As is shown in FIGS. 2 and 8, the preferred means of this sensor field separation takes the form of a masking strip 56, provided along one side of drip chamber 6 in confronting relation with detectors 14 and 18. A pair of horizontal, generally rectangular slits 58 and 60 are formed in masking strip 56 at vertically spaced locations so as to be in horizontal alignment with detectors 14 and 18, and interposed between those detectors and the adjacent side wall of drip chamber 6. Slits 58 and 66 define the field of sight of detectors 14 and 18. The slits 58 and 60 contribute to the assurance that detectors 14 and 18 will sense only straight, linear fields generated by light sources 12 and 16. Fields 48 and 50 are shown in FIG. 2 in the preferred rectangular form, as viewed by detectors 14 and 18. Thus, fields 48 and 50, as viewed by the two detectors, each have generally straight, horizontal upper and lower boundaries. Masking strip 56, with slits 58 and 60, thus insures that detectors 14 and 18 will accurately detect a drop entering and leaving each of the vertically spaced sensor fields 48 and 50. The height of slits 58 and 60, measured along the vertical extent of drop chamber 6, is exaggerated for clarity on the enlarged scale of FIG. 2. The slits are shown closer to relative size in FIG. 8. The mask 56 with slits 58 and 60 could be positioned in front of the emitters 12 and 16, or in front of the detectors 14 and 18 as shown, or in front of both. The detectors and emitters may be mounted in any convenient way, a plexiglass support of generally arcuate shape around the outside of the generally cylindrical drop chamber 6 having been found to be satisfactory. In actual practice, slits 58 and 60 generally have such a height dimension so as to be small compared to a drop diameter or vertical dimension. The height of the first sensor field 48 is indicated in FIG. 2 by dimension "a," and the height of the lower sensor field 50 is indicated by vertical dimension "c." The vertical dimension "b" indicates the distance between the upper extremity of first field 48 and the lower extremity of second field 50.

The vertical dimension "h" indicates the vertical distance between the center of a drop entering the first field 48, and the center of that same drop as it exits field 48. Similarly, vertical dimension "i" indicates the vertical distance between the center of a drop entering bottom field 50 and the center of that drop exiting field 50. The vertical dimension "f" indicates the vertical distance between the center of a drop entering the top field 48 and the center of that drop exiting the bottom field 50.

An algorithm has been developed for determining drop size and volume, utilizing the time the drop takes to travel through each sensor field (dimensions "h" and "i") and through both sensor fields (dimension "f"), together with the known sensor field widths and the distance from the start of one field to the end of the other. The elapsed time for a drop to travel through each and both of the two fields is determined by timers actuated by the IR detectors 14 and 18. When a drop enters the first field 48, its IR detector(s) 14 generates a signal which is monitored by a comparator means 54, preferably in a Schmitt Trigger configuration, as hereinafter described with respect to the FIG. 4 preferred control circuitry. The output of the Schmitt Trigger starts a counter when the drop enters the field. The counter is stopped when the drop leaves the field. The time related to the count on the counter is the time, within some error bounds determined by the rate of counting, for the drop to travel the distance of the field width "a," plus the drop height D, minus the fraction of a drop required to trigger the comparator. This signal generation process also applies to the second field 50 and the distance C. Similarly, the time measured over the distance "b" is the time for the drop to travel the known distance from the start of the first field to the end of the second, plus the drop height D, minus the fraction of the drop that is needed to trigger the comparators. These descriptions apply to the equations:

$$h = a + D - (D_{H1} + D_{L1})$$

$$i = c + D - (D_{H2} + D_{L2})$$

$$f = b + D - (D_{H1} + D_{L2})$$

and their related times $t_h$, $t_i$ and $t_f$, wherein $D_H$ represents the fraction of D to trigger drop presence, $D_L$ represents the fraction of D to trigger drop absence, and the subscripts "1" and "2" refer to the first and second sensor fields, respectively.

To estimate drop size, the first field 48 is preferably positioned far enough below the drop orifice 52 so that the drop does not enter the field until it is in free fall. The second field 50 is preferably above the fill line 54 of the drip chamber far enough not to be obstructed by waves or small splashes created when the drop hits the fluid reservoir at the bottom of the drip chamber. With the fields in these positions, the average velocity through each of the two sensing fields is preferably computed by the equations:

$$V_h = h/t_h$$

$$V_i = i/t_i$$

Because the acceleration of the drop is linear, the average velocity of the drop through both fields, $V_f$, is equal to the average of the average velocities of the drop through each of the fields and may be written:

$$V_f = (\tfrac{1}{2})(V_h + V_i)$$

From this value of average velocity an accurate estimate of "f" may be obtained as follows:

$$f = V_f t_f = (\tfrac{1}{2})(V_h + V_i) t_f = b + D - (D_{H1} + D_{L2})$$

so: $D = \frac{1}{2}tf(V_hV_i) - b + D_{H1} + D_{L2}$, where D is the vertical dimension of the drop.

In the ideal case, $D_H$ and $D_L$ are negligible.

To determine drop volume, utilizing the vertical dimension D of the drop, it is preferable to make certain simplifying assumptions about the behavior of the drops and the forces acting on them as they fall. While any number of assumptions may be made, generally only the following three assumptions are pertinent. The following assumptions are based on the fact that the drops travel only about 2.5 cm before reaching the fluid reservoir 54 in the closed environment of the drip chamber. The first assumption is that the acceleration of the drops is linear, regardless of any initial velocity, because the drops never reach terminal velocity Secondly, the shape of the drop is determined more by surface tension than by air friction. This implies that the drops are basically spherical in shape. The drops are assumed to oscillate slightly due to their release from the drop orifice 52. Third, air resistance is not a significant force on the drops. This assumption attributes the behavior of the falling of a drop solely to the initial velocity and the acceleration of the drop due to gravity.

The validity of the first and third assumptions has been confirmed mathematically utilizing basic equations for drop terminal velocity and the force due to drag friction Terminal velocity may be determined by the equation:

$$V_T = (2mg/C_D A_p d)^{\frac{1}{2}}$$

where m is the drop mass, g is the acceleration due to gravity, $C_D$ is the coefficient of drag, $A_p$ is the projected area of the drop, and d is the density of air. The time it would take a drop to reach terminal velocity may be approximated by the equation $$t_T = g/V_T$$

The distance the drop will travel before reaching terminal velocity is approximated by the equation $$d_T = (\frac{1}{2})g t_T^2$$

A drop of water 0.5 cm in diameter will reach terminal velocity after about 1060 cm of free fall. The larger drops will reach terminal velocity before the smaller drops when air friction is considered. This calculation supports the first assumption by showing that a drip in a drop chamber travels only about 0.25% of the distance necessary to attain terminal velocity.

The force due to drag friction may be calculated from the equation:

$$F_D = (\frac{1}{2})C_D A_p d V^2$$

Where V is the velocity of the drop. This equation was used to check the validity of the third assumption. The results of the calculations show that the force due to drag friction is less than 0.5% of the force due to gravity. This result indicates that drag force does not significantly effect the rate at which a drop will fall. The first and third assumptions of falling drops are valid, based on the above calculations.

The validity of the assumption that a drip falling in a drop chamber is basically spherical has been determined qualitatively.

Using the above assumptions, and the determined value of the vertical dimension D of the drop from the aforesaid algorithm, drop volume may be determined. Based on a spherical drop model, the vertical drop dimension D will be the diameter of a spherical drop, and drop volume may be determined using the formula for the volume of a sphere, as hereinafter set forth.

It is noteworthy that the foregoing preferred assumptions made about drop characteristics used to determine drop volume from drop size are independent of the drop size estimation technique. Specifically, the above-described drop size estimation algorithm is not based in any way on the assumption that the drops are spherical. This algorithm will estimate the effective size of any particle in the dimension parallel to the force of gravity. Variations in the model of the drop may be made without affecting drop size, because the size measurement algorithm is independent of drop shape.

The preferred hardware utilized to implement the size measurement algorithm generally starts with the light emitting diodes 12 and 16, and their respective detectors 14 and 18 which create the sensor fields 48 and 50, as described above with respect to FIG. 2. The greatest change in the output of detectors 14 and 18 caused by the passing of a drop, occurs when the drop interrupts the direct transmission from emitter to detector. The output signals of the IR detectors resulting from drops from the 60 drop per milliliter tube sets and the 15 drop per milliliter tube sets differ only in the duration of the signals.

Figure 4:
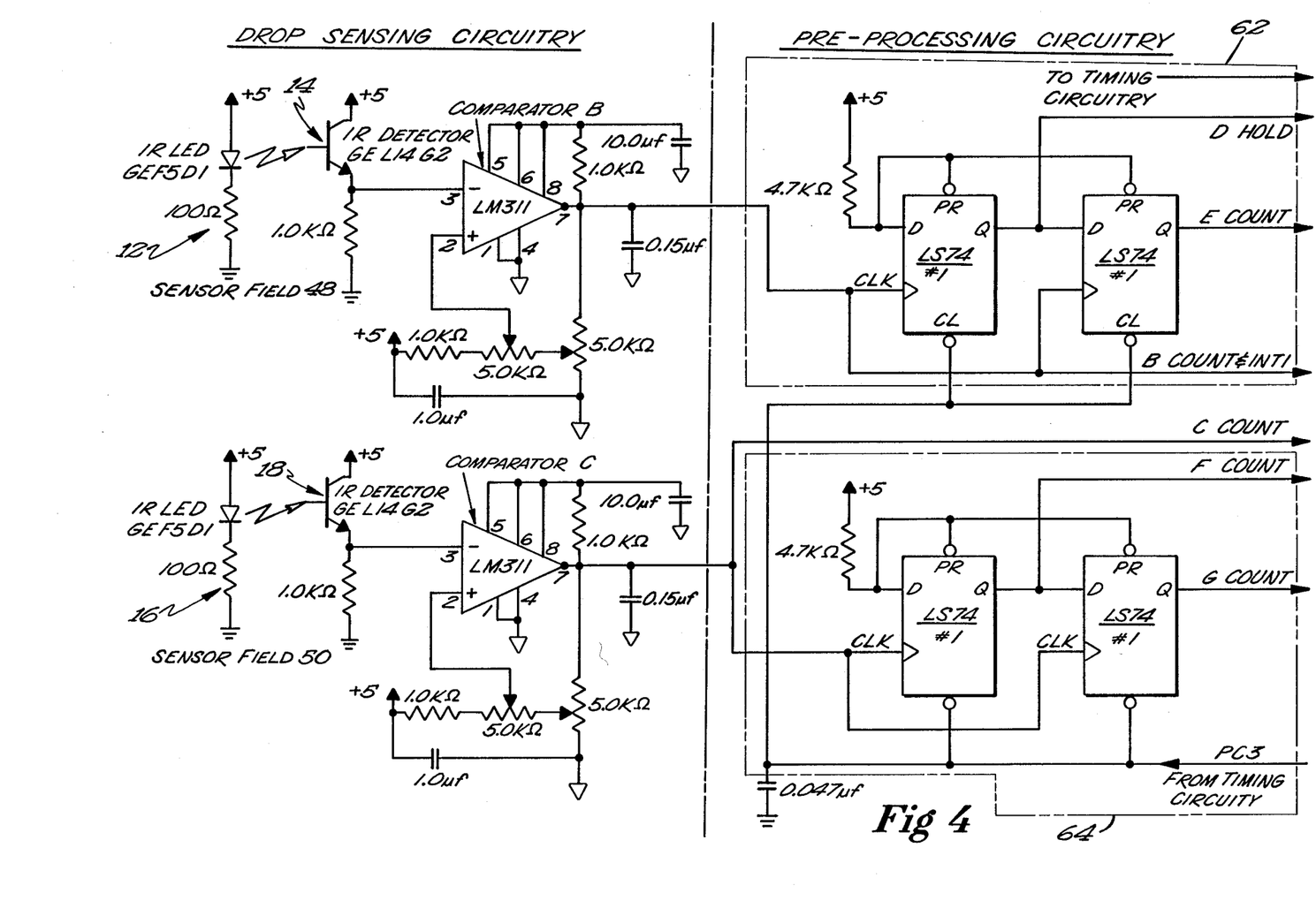
FIG. 4 is a diagram of a representative signal conditioning circuit, which receives input signals from the drop sensors.

The output from each detector 14 and 18 is an input for one of two Schmitt trigger comparator configurations designated as B and C in FIG. 4. These devices compare the voltage output of the detectors to a preset reference voltage. The output of an IR detector in the "no-drop" condition to a Schmitt comparator in the configuration of the prototype is greater than the reference voltage in the preferred circuit embodiment, causing the comparator to hold its output low at ground potential (0 volts). When the input drops below the reference, the output changes to a high positive, preferably on the order of five (+5) volts. The output moves back to ground after the drop passes and the input is again above the reference voltage. Small oscillations of the drops as they enter a sensor field is one source of noise. A drop will oscillate in and out of a sensor field very quickly as it first enters the field, before it totally interrupts the field. This in turn causes the output of an IR detector to dip momentarily below its "no-drop" level, causing the comparator output to switch levels. Two other sources of false triggers are small fluid droplets that occasionally splash up after the drop has fallen, and a small drop "tail" that is formed immediately after release from the drop orifice None of these noise sources completely disrupts the fields, so the amplitudes of the outputs of the detectors are not as extreme as they are for true drops. Preferably, $V_{LH}$ is set lower than $V_{HL}$ so that only true drops may trigger the initial transition, and most of the drop will be out of a field before the comparator output returns to the "no-drop" state. The time it takes the drop to alter the IR detector output to below $V_{LH}$, and the time the drop is still in the field after $V_{HL}$ has been reached, are the trigger delay times The preferred Schmitt comparator configuration converts the analog output from an IR detector into the low and high digital signals needed to trigger the necessary timing functions Occasionally, splashes or drop tails will trigger false timing signals, but a controlling system algorithm may be written to ignore these extraneous signals.

The difficulty of processing these signals becomes evident when a clear fluid, such as water, is dropped through the sensor fields. As the drop falls, the edges of the drop refract the IR field as expected, but the center area of the drop acts as a magnifying lens, amplifying the transmitted IR signal The amplified portion of the transmitted signal is greater than the above defined VHL reference voltage, causing a momentary "no-drop" output. This "clear fluid" glitch is of different time duration for the 15 and 60 drop/ml tube sets, because of the difference in drop size Also, the "clear fluid" glitch does not often appear in the second sensor field when a 60 drop/ml tube set is used.

Discrete logic circuitry is the preferred method of consistently and successfully eliminating errors due to the "clear fluid" glitch. However, there may be a processor fast enough to allow an algorithm to filter the "clear fluid" glitch. The preferred discrete logic circuitry is further described below.

Figure 5:
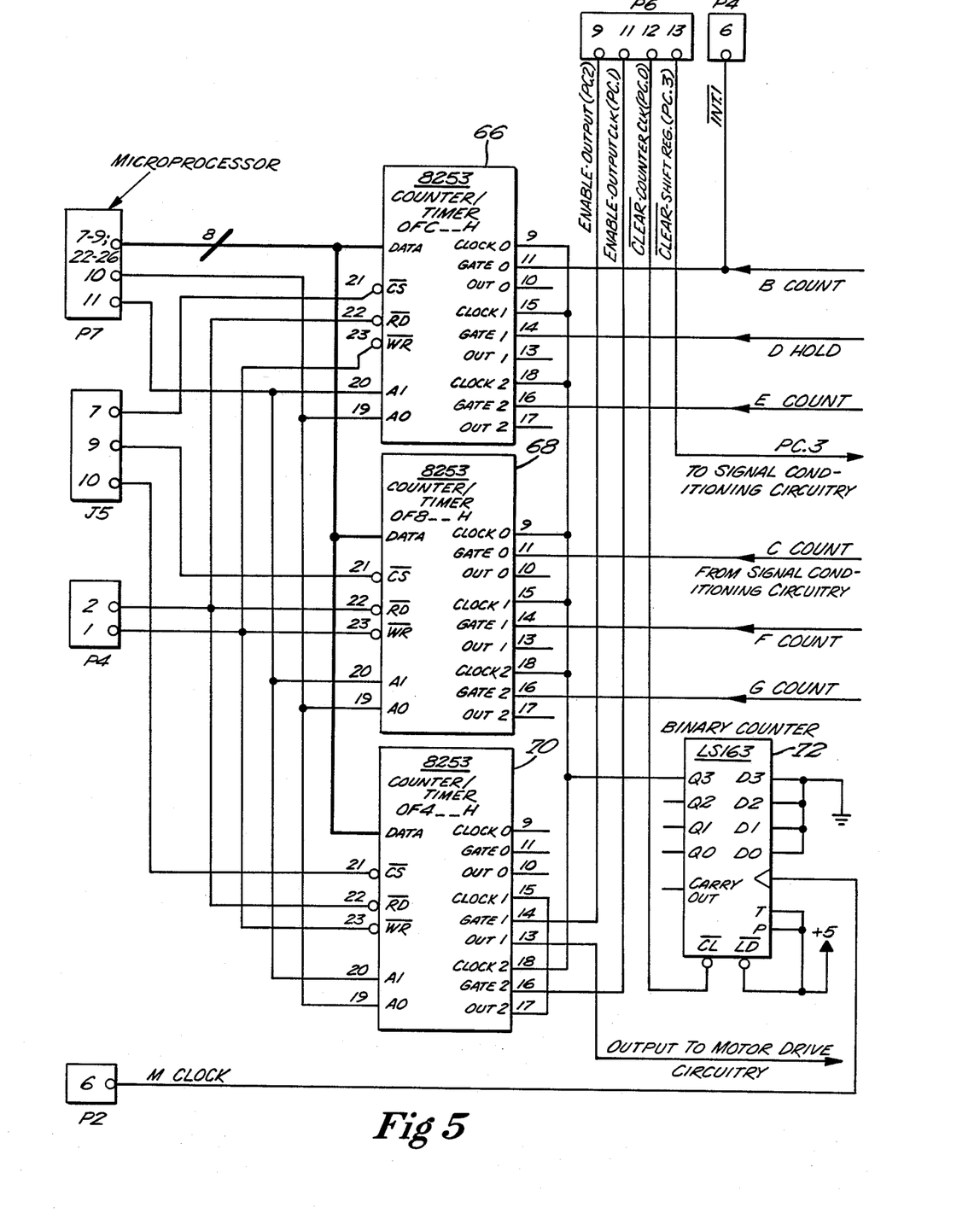
FIG. 5 is a diagram of a representative timing circuit.

As may best be understood by reference to FIG. 4, for each comparator output, a means as represented by a 74LS74 dual, positive edge triggered, D-type flip-flop acts as a 2-bit shift register 62 and 64, clocked by the comparator. Initially, the bits of the shift registers are cleared to zero volts by a signal preferably generated by the chosen CPU. This signal is referred to as PC.3 in FIGS. 4 and 5 and drives all of the clear pins (CL) of both shift registers. The outputs of both comparators and both bits of both shift registers are used as timing triggers for timers 66 and 68 (FIG. 5). If the timers controlled by the second bit of the shift registers read zero, the glitch did not take place, and processing the time information takes one form. If either of these two timers is not zero, then a "clear-fluid" glitch occurred in one of the sensor fields, and must be accounted for. The corrections for the "clear-fluid" glitch take place in the size estimation section of the software and are hereinafter discussed.

Each of the six outputs from the comparators and shift registers is used as the gate signal to one of the three counters on each of two 16-bit programmable, count-down counter/timers 66 and 68, as shown in FIG. 5 Intel 8.253 or any comparable, commercially available counter/timers may be used. On the positive edge of these signals, a count of 0FFFF hex (65535 decimal) is loaded into the counters The counters count while their gates are at a logical high and stop counting when their gates return to a logical low. The rate of counting is preferably determined by dividing the central processing unit (CPU) clock by some factor and feeding the clock inputs of all the counters on the first two counters 66 and 68. The CPU clock may be divided by a means similar to a 740LS163 binary counter. A fast clock input is necessary to achieve the temporal resolution required to determine vertical drop size.

The counts from these counters are read by the CPU (24) and converted to times, sizes and eventually volumes, preferably by the software, as described below in connection with the application of the above-described drop size estimation algorithm. The estimates of drop volume are multiplied by the drop rate to determine the actual flow rate of the system. Drop rate is presently monitored by an internal clock of the CPU utilizing signals from the first drop sensor field 14, but may also be monitored by an external counter/timer. The CPU then compares this volume flow rate information with the desired volume flow rate, to determine if the flow controlling motor rate and/or direction should be altered. If the motor rate or direction needs to be adjusted, the CPU, 24, determines what the adjustment should be, and provides an appropriate adjustment signal input to the motor drive circuitry as indicated diagrammatically in FIGS. 1 and 6.

Figure 6:
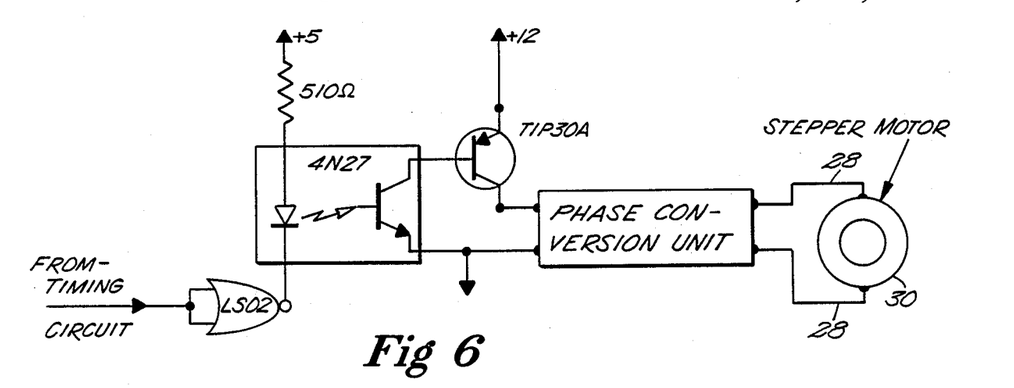
FIG. 6 is a diagram of a representative motor drive circuit.

After the CPU has computed the new pump motor adjustment, the CPU determines how much the output counter must count in order to produce the proper motor step frequency to attain the desired, adjusted motor control. This number is inputted into one of the counters of another counter/timer 70 and its output square wave is used to drive the circuitry which runs the motor 30 (FIG. 6). One satisfactory arrangement for drive circuitry starts with a discrete NOR logic gate, 74LS02, acting as buffer for the counter, driving the light emitting diode (LED) side of a photon coupled optoisolator, such as a General Electric 4N27 optoisolator. The phototransistor side of the optoisolator drives a power transistor, TIP30A, which provides the larger voltage and current needed to trigger the presently used stepper motor driver.

The programmed CPU implements all of the control functions necessary to operate the timing circuitry described above with respect to FIG. 5. The CPU also takes the counts from the programmable counters, converts them to values of time, computes the vertical dimension D of the drop in the direction of fall according to the above described algorithm, and calculates the drop volume. A calibration factor is applied, as hereinafter explained, to account for system artifacts, such as trigger delay time, as well as errors in the drop model representing deviations in the drop model from a purely spherical shape towards an ellipsoid. The general flow diagram of the program logic steps is shown in FIG. 7.

Figure 7:
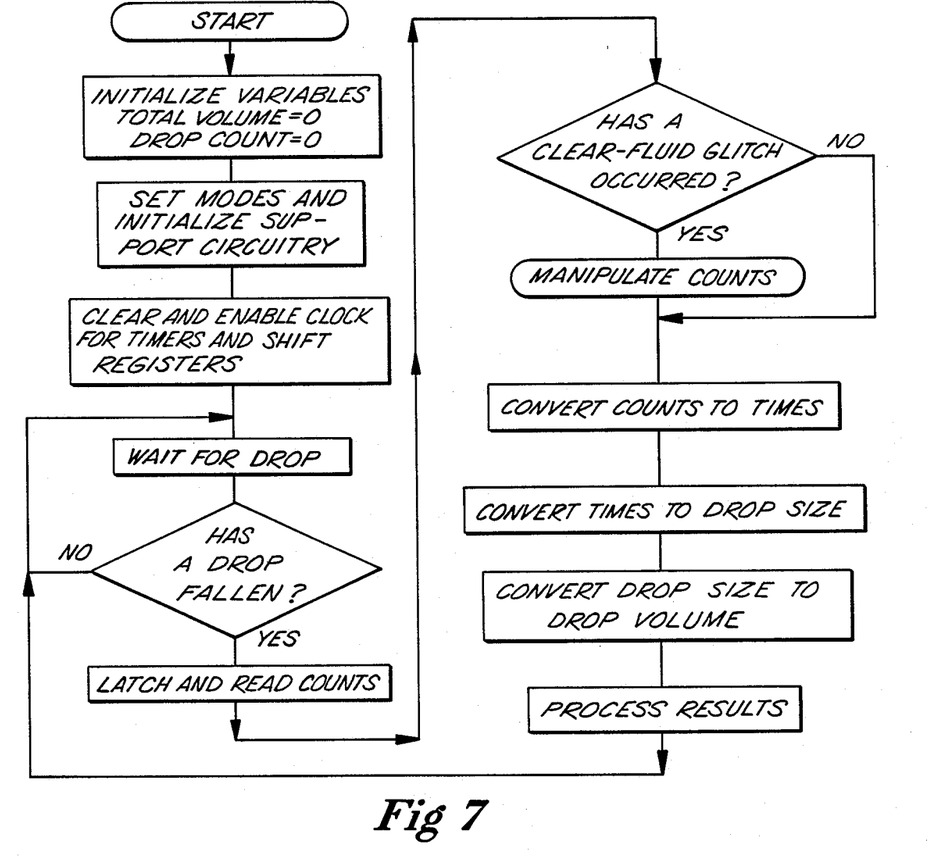
FIG. 7 is a logic diagram of a representative program used to operate the control circuitry and to provide the desired drop volume and volumetric flow rate information.

As seen in FIG. 7, after initializing the timing variables, the program sets the modes of an input/output microprocessor interface and the modes of the programmable, count down counter/timers 66, 68 and 70.

As described above with respect to FIGS. 4 and 5, the six timing signals generated as a drop passes through the two sensor fields 48 and 50 are used as gate signals for the six counter/timers 66 and 68, set to the proper mode by the CPU. An interrupt signal is sent to the CPU 24, (FIG. 1) on the first falling edge of the gate signal from the first comparator B (FIG. 4). This signal tells the CPU to interrupt what it is doing (idling) and perform a special interrupt subroutine. By the time the interrupt routine begins, the drop has generally passed through the first field 48 and is almost in the second field 50. The interrupt routine reads the count of the timer 66 relating to the first field 48 giving the drop enough time to pass through the second field 50. The interrupt routine then latches the count of the shift register 62 of the first field, preventing any alterations of the true count by drop tails or splashes. The interrupt routine then clears and disables the shift registers with PC.3, preventing any further changes in the counts associated with the shift registers of the second field 50.

The interrupt routine then checks to see if the count related to the second bit of either shift register is not zero. If either one of these counts is not zero, a "clear fluid" glitch occurred in the field with which the shift register is associated, as explained above. To account for this glitch, the CPU subtracts the counts controlled by the outputs of the comparators from the counts controlled by the second bit of the shift registers. The resulting counts are the counts from the end of the comparator gate signal to PC.3, the "clear shift register" signal. These counts are then subtracted from the count triggered by the first bit of their respective shift registers. These computed counts represent the actual time the drop spent traveling through sensor fields 48 and 50. The resulting count from the first subtraction of the counts associated with the second field 50 is subtracted from the count triggered by the first bit of the shift register associated with the first field 48. The resulting count represents the actual time the drop took to travel through both fields.

The gathered counts are then converted to values of time. This conversion is accomplished by dividing the counts by the frequency of the clock pulses driving the counter/timers These values of time, the field widths, and the distance through both fields are then used to compute the vertical drop dimension D based on the drop size estimation algorithm derived above. This vertical drop dimension D is converted to drop volume by assuming the shape of the drop. If the drop is assumed spherical, the vertical drop size D becomes equivalent to the diameter of the sphere and the drop volume is determined by the equation:

$$\text{Volume} = (Pi/6)D^3$$

In reality, the drop may not be a perfect sphere. Both drop oscillations and air friction slightly alter the spherical shape of the drops. Air friction slightly elongates falling drops as it tries to form the drops into the tear-shape that follows the lines of air flow. A drop volume estimate will be larger than its actual volume if the drop is more eliptical than spherical. Accordingly, a correction factor is entered into the derivation of drop volume to account for errors caused by deviations of the drop from a spherical shape towards that of an elipse. In order to calculate the correction factor, a water test is conducted. Correction factors may be determined by allowing fluid to flow through the IV tube set from the liquid supply container 4, FIG. 1. The fluid flowing out of the tube set is collected in a graduated cylinder, so as to be able to determine the actual volume of fluid dispensed. Simultaneously, the volumetric drop detection system is actuated, and the CPU reports the total number of fallen drops, determines the vertical drop dimension D in accordance with the above-described algorithm, and estimates the drop volume utilizing the volume of a sphere. The CPU may also add the volume of each drop to the previous cumulative drop volume, which is initially zero, and print out the cumulative volume, as well as individual drop volumes Such information may be visually presented, as by the display 25 shown in FIG. 1. The amount of water collected in the graduated cylinder is compared to the cumulative volume as kept by the CPU. In this way, a calibration factor "f" is arithmetically determined. This correction factor also accounts for other system artifacts such as trigger delay, error in field width sizes, and errors in the distance between each field. Such a correction factor is incorporated in the program of the CPU and is utilized as a multiple in the equation $D = D \times f$. The CPU may then use the corrected value of D in calculating drop volume utilizing the aforesaid formula for the volume of a sphere.

The volumetric flow rate measurement technique described herein, based on estimating individual drop volume, is accurate when the proposed drop model is used in conjunction with correction factors, which account for trigger delay errors and other errors generated by system artifacts. The developed volumetric flow rate measurement technique has been utilized with a closed loop, digital, integral control system and shown to control volumetric flow rate to within +5% error, when properly calibrated, and may therefore be used with emergency hospital equipment.

The volumetric infusion delivery system, utilizing the disclosed volumetric flow rate measurement technique, accurately works noninvasively with standard IV tube sets, thereby lowering operating costs below those of presently available systems. Operating costs will be lower because systems using the disclosed technique avoid the costly, dedicated IV tube sets required for presently available systems by working with the less expensive standard IV tube sets.

In the preferred embodiment, all of the control circuitry, including the shift registers and timer/counters, as described herein, may be incorporated into a microprocessor chip contained within the housing of the volumetric flow regulating device 32. Hence, as is indicated in FIG. 1, all of the control circuitry is indicated by reference numeral 32', indicating its incorporation within the housing 32.

It is also anticipated that variations may be made in the hardware and control circuitry without significantly impacting the successful operation of the drop detection and volumetric flow rate measuring and control system disclosed herein For example, other forms of comparators, other than that of the Schmitt trigger disclosed herein, may be utilized. Also, it is contemplated that a single light source, rather than the two infrared light emitting diodes (IRLED), could be utilized in conjunction with a pair of vertically based drop sensors 14 and 18, as described with respect to FIG. 2.

Although the system has been described with respect to the automatic control of the delivery of intravenous fluids to patients utilizing standard IV administration sets, the system and apparatus provides an improved and effective means for measuring volumetric flow rate, utilizing the drop detection system, which is applicable to the measurement of volume or volumetric flow rate of other fluids. For example, a useful application would be in the volumetric flow control of waste materials in fluid form in biomass conversion processes, where accurate control of volumetric flow rates of nutrients and bacteria is critical In any application, either one of the two vertically spaced drop sensors 14 and 18 may be utilized to determine drop rate; the upper or first drop sensor 14 is preferably relied upon for that purpose.

It is contemplated that these and other variations in the hardware and circuitry of the drop detection and fluid volume measuring and control system disclosed herein may be made without departing from the spirit and scope of the invention as defined in the following claims.

I claim:

1. Intravenous fluid delivery apparatus of the type comprising a fluid container, a transparent drip chamber connected to the outlet of said fluid container, a length of flexible tubing attached in fluid flow communication between the discharge side of said drip chamber and injection means for intravenous fluid introducing into a patient, wherein the improvement comprises:

flow regulating means operatively associated with said flexible tubing for regulating the flow of intravenous fluid through the delivery apparatus;

drive means for said flow regulating means;

a drop orifice at the top of said drip chamber opening freely into unobstructed interior space of said drip chamber, said drip chamber being a standard, commercially available device having a such a width between laterally spaced side walls separated by an uninterrupted space that drops sequentially formed one at a time at said drop orifice may freely fall through said drip chamber without contact with an confining wall surface;

first sensor means positioned in proximity to said drip chamber for sensing drop presence and emitting a first signal in response thereto, said first sensor means comprising a first light emitting source generating a first sensing field projecting generally transversely across said drip chamber and an aligned light detector, said first light source and its generated sensor field being so positioned a predetermined distance below the outlet of said drop orifice that each separate drop does not enter the first sensing field until the drop is in free fall;

second sensor means positioned in proximity to said drip chamber for sensing drop presence and emitting a second signal in response thereto, said second signal being utilized in cooperated with said first signal to determine a drop size dimension, and said second sensor means comprising a second light emitting source generating a second sensing field projecting generally transversely across said drip chamber and a second light detector in alignment therewith, said second light source being vertically spaced below said first light source a predetermined distance along the height of said drip chamber, whereby two vertically spaced sensor fields are established;

timer means operatively associated with said first and second sensor means to receive signals therefrom to measure the elapsed time for each drop to pass through each of said two sensor fields and through a known vertical distance between the fields, as an indication of the vertical drop size dimension in the direction of drop free fall;

circuit means incorporating said drive means and said first and second sensor means and said timer means, said circuit means further comprising electronic processor means programmed to calculate the actual volumetric flow rate of fluid, based on a multiplication function of drop rate as indicated by the number of drops sensed by either said first or second sensor means in a unit of time and drop volume as a function of said drop size dimension, and comparator means for comparing said actual volumetric flow rate to a predetermined, desired volumetric flow rate; and drive signal generating means in said circuit connected to said drive means for producing a drive signal based on the output of said comparator means to adjust said drive means as necessary to maintain a predetermined flow rate.

2. Intravenous fluid delivery apparatus as defined in claim 1 wherein:
said flow regulating means comprises a peristaltic pump.

3. Intravenous fluid delivery apparatus as defined in claim 2 wherein:
said drive means comprises a stepper motor.

4. Intravenous fluid delivery apparatus as defined in claim 1 wherein:
said flow regulating means comprises a valve in the form of clamping means acting on said flexible tubing to regulate the flow therethrough.

5. Intravenous fluid delivery apparatus as defined in claim 1 wherein:
said electronic processor means comprises a microprocessor.

6. Intravenous fluid delivery apparatus as defined in claim 1 wherein:
said electronic processor means is programmed to explicitly determine the vertical size dimension of a drop according to the typical formula:

$$D = \tfrac{1}{2} t_f (V_h + V_i) - b + D_H + D_L$$

wherein:
$D$ = the vertical dimension of a drop;
$t_f$ = the measured time for a drop to pass completely through the two sensor fields;
$V_h = h/t_h$, where h is the vertical distance from the center of a drop entering the first sensor field to the center of that drop leaving that field, and $t_h$ is the measured time for a drop to travel through distance h;
$V_i = i/t_i$, where i is the vertical distance from the center of a drop entering the second sensor field to the center of a drop leaving that field, and $t_i$ is the measured time for a drop to travel through distance i;
b = the total vertical distance from the top of the first sensor field to the bottom of the second sensor field;
$D_H$ = the fraction of D to trigger drop presence in the first sensor field; and
$D_L$ = the fraction of D to trigger drop exit from the second sensor field.

7. Apparatus for measuring the volumetric flow rate of a fluid passing through a transparent drip chamber having fluid inlet means at its upper end and fluid outlet means at its lower end, said apparatus comprising:

a drop orifice at the top of said drip chamber opening freely into unobstructed interior space of said drip chamber, said drip chamber having a width between laterally spaced side walls separated by an uninterrupted space such that drops sequentially formed one at a time at said drop orifice may freely fall through said drip chamber without contact with any confining wall surface;

first sensor means positioned in proximity to said drip chamber for sensing drop presence and emitting a first signal in response thereto, said first sensor means comprising a first light emitting source noninvasively located externally of said chamber and generating a first sensing field projecting generally transversely across said drip chamber and an aligned light detector positioned outside of said chamber, said first light source and its generated sensor field being so positioned a predetermined distance below the outlet of said drop orifice that each separate drop does not enter the first sensing field until the drop is in free fall;

second sensor means positioned in proximity to said drip chamber for sensing drop presence and emitting a second signal in response thereto, said second signal being utilized in cooperation with said first signal to determine a drop size dimension, said second sensor means comprising a second light emitting source noninvasively positioned externally of said chamber and generating a second sensing field projecting generally transversely across said drip chamber and a second light detector in alignment therewith outside of said chamber, said second light source being vertically spaced below said first light source a predetermined distance along the height of said drip chamber, whereby two vertically spaced sensor fields are established utilizing any commercially available drip chamber;

circuit means for receiving the signals emitted by said first and second sensor means, comprising means for determining a drop size dimension based on a predetermined time correlation of and between said signals for a specific drop, and means for determining the volumetric flow rate based on the number of drops sensed by either the first or second sensor means in a unit of time and the determined drop size dimension; and said means for determining a drop size dimension comprises timer means operatively associated with said first and second sensor means to receive said first and second signals therefrom and functioning to determine the vertical dimension of a drop in the direction of drop passage through said drip chamber based on the time duration of said first and second signals as a measure of the time for a specific drop to pass through each of said two sensor fields and on the time interval for a specific drop to pass through a predetermined distance between the two sensor fields.

8. Apparatus as defined in claim 7 wherein:
said means for determining the drop size dimension and the volumetric flow rate comprises electronic processor means programmed to determine the volume of a drop based on said drop size dimension as a step in determining volumetric flow rate.

9. Apparatus as defined in claim 8 wherein:
said electronic processor means comprises a microprocessor.

10. Apparatus as defined in claim 7 wherein:
said first and second sensing fields are vertically spaced apart a predetermined distance greater than the vertical dimension of a drop in free fall and through which distance separate and distinct drops sequentially formed at said drop orifice may freely fall in passing from said first field into and through said second field.

11. Apparatus as defined in claim 7 and further including:
a masking strip positioned externally of said drip chamber and having first and second vertically spaced slits therein located in horizontal alignment with said first and second sensing fields respectively to thereby define said first and second sensing fields of a finite height and with discrete top and bottom boundaries as viewed by said first and second light detectors, whereby each of said first and second light detectors is activated for the duration of the time period that each separate drop is in interrupting contact with each sensing field.

12. A process for measuring the volume of a drop of a liquid utilizing a transparent drip chamber comprising the steps of:

generating a first sensing field generally transversely of a transparent drip chamber by a first light emitting source aligned with a first light detector;

simultaneously generating a second sensing field generally transversely of said transparent drip chamber at a predetermined, vertically spaced location below said first sensing field by a second light emitting source aligned with a second light detector at said vertically spaced location;

introducing discrete drops of liquid sequentially into the unobstructed, open space of said drip chamber from the top of said chamber so that the drops fall one at a time through said first and second sensing fields in an unconfined, free falling state;

producing a first signal in response to the passage of a specific, free falling drop into and through said first sensing field;

producing a second signal in response to the subsequent passage of said specific, free falling drop into and through said second sensing field; and measuring the time duration of said first and second signals and the time interval between the start of said first signal and the end of said second signal for said specific, free falling drop and thereby determining the vertical dimension of said specific drop in the direction of drop fall through said chamber based on a predetermined algorithm utilizing said time measurements, and thereafter calculating the volume of said drop utilizing said vertical drop dimension.

13. The process for measuring the volume of a drop as defined in claim 12 wherein:
said first and second sensing fields are generated and detected by said first and second light detectors as having a finite, predetermined height in the direction of drop fall, and said predetermined height of each field and the predetermined vertical distance between said fields are utilized in said algorithm in conjunction with said time measurements, indicative of the time for a specific drop to pass through each of said first and second fields as well as the time for the drop to pass through a known vertical distance between the fields to determine said vertical drop dimension.

14. The process for measuring the volume of a drop as defined in claim 13 wherein: said algorithm comprises the typical formula:

$$D = \tfrac{1}{2} t_f(V_h + V_i) - b + D_H + D_L$$

wherein:
D = the vertical dimension of a drop;
$t_f$ = the measured time for a drop to pass completely through the two sensor fields;
$V_h = h/t_h$, where h is the vertical distance from the center of a drop entering the first sensor field to the center of that drop leaving that field, and $t_h$ is the measured time for a drop to travel through distance h;
$v_i = i/t_i$, where i is the vertical distance from the center of a drop entering the second sensor field to the center of a drop leaving that field, and $t_i$ is the measured time for a drop to travel through distance i;
b = the total vertical distance from the top of the first sensor field to the bottom of the second sensor field;

$D_H$ = the fraction of D to trigger drop presence in the first sensor field; and $D_L$ = the fraction of D to trigger drop exit from the second sensor field.

15. The process for measuring the volume of a drop as defined in claim 13 wherein:

the known vertical distance between the fields through which drop passage time is measured is that from the top of the first field to the bottom of the second field.

16. The process as defined in claim 12 wherein said process further comprises:

determining the drop rate in number of drops per unit of time based on signals emitted by one of said sensor means; and multiplying said drop volume and drop rate values and thereby determining volumetric flow rate.

17. The process as defined in claim 16 and further comprising:

comparing said volumetric flow rate with a predetermined flow rate; and controlling the flow rate of said fluid by adjustment of a flow regulating mechanism in response to the determined difference between said determined and predetermined flow rates.

* * * * *

UNITED STATES PATENT AND TRADEMARK OFFICE
CERTIFICATE OF CORRECTION

PATENT NO. : 4,820,281

DATED : April 11, 1989

INVENTOR(S) : Casimir E. Lawler, Jr.

It is certified that error appears in the above-identified patent and that said Letters Patent is hereby corrected as shown below:

Col. 7, line 8, change "32,," to --32',--
Col. 11, line 27, change "friction Terminal" to --friction. Terminal--
Col. 12, line 67, change "functions Occasionally" to --functions. Occasionally--
Col. 13, line 8, change "IR signal The" to --IR signal. The--
Col. 13, line 13, change "drop size Also" to --drop size. Also-
Col. 13, line 45, change "Fig. 5 Intel" to --Fig. 5. Intel--
Col. 15, line 16, change "timers These" to --timers. These--
Col. 15, line 51, change "volumes Such" to --volumes. Such--
Col. 16, lines 5 and 6
Line 5, change "shown to
              control" to --shown to control--
Col. 16, line 31, change "herein For" to --herein. For--
Col. 16, line 50, change "critical In" to --critical. In--

Claim 1, col. 17, line 11, change "on at a time" to --one at a time--
Claim 1, col. 17, line 28, change "cooperated" to --cooperation-
Claim 14, col. 20, line 47, change "wherein: said" to --wherein: said--

Signed and Sealed this

Twenty-first Day of November, 1989

Attest:

JEFFREY M. SAMUELS

Attesting Officer     Acting Commissioner of Patents and Trademarks